United States Patent [19]
Brown

[11] Patent Number: 5,945,337
[45] Date of Patent: *Aug. 31, 1999

[54] METHOD FOR CULTURING CD34+ CELLS IN A SERUM-FREE MEDIUM

[75] Inventor: Ronald L. Brown, Derwood, Md.

[73] Assignee: Quality Biological, Inc., Gaithersburg, Md.

[*] Notice: This patent is subject to a terminal disclaimer.

[21] Appl. No.: 08/953,434

[22] Filed: Oct. 17, 1997

Related U.S. Application Data

[60] Provisional application No. 60/028,152, Oct. 18, 1996.

[51] Int. Cl.$^6$ .................................................. C12N 5/02
[52] U.S. Cl. ..................... 435/389; 435/384; 435/404; 435/405; 435/407
[58] Field of Search .................................. 435/389, 404, 435/383, 384, 405, 407

[56] References Cited

U.S. PATENT DOCUMENTS

| | | |
|---|---|---|
| 4,560,655 | 12/1985 | Baker . |
| 4,808,611 | 2/1989 | Cosman . |
| 4,927,762 | 5/1990 | Darfler . |
| 5,021,349 | 6/1991 | Drouet et al. . |
| 5,061,620 | 10/1991 | Tsukamoto et al. . |
| 5,397,706 | 3/1995 | Correa et al. ................ 435/241.31 |
| 5,405,772 | 4/1995 | Ponting I.L.O. ............... 435/240.31 |
| 5,409,825 | 4/1995 | Hoffman et al. . |
| 5,468,635 | 11/1995 | Komiya et al. ................ 435/240.21 |
| 5,635,387 | 6/1997 | Fei et al. . |

FOREIGN PATENT DOCUMENTS

| | | |
|---|---|---|
| WO 95/02685 | 1/1995 | WIPO . |
| 95/06112 | 3/1995 | WIPO . |

OTHER PUBLICATIONS

Smith et al., "Neutrophil maturation of CD34+cells from peripheral blood and bone marrow in serum–free culture medium supplemented with G–CSF", 37 th Annual Meeting of the American Society of Hematology, Seattle, WS, USA, Dec. 1–5, 1995. Blood Dexter et al., "Growth and Differentiation in the Hemopoietic System", In: Annual Review of Cell Biology, Ed. by G.E. Palade, 1987, vol. 3, pp. 423–441.

Brandt et al., "Characterization of human hematopoietic stem cells" In: The Biology of Hematopoiesis, Ed. by Dainiak et al. Wiley–Liss, NY, 1990, pp. 29–36.

Quality Biological, Inc., Catalogue Page 57 for QBSF–58 (1995).

Sigma Catalog, p. 197 (1998).

Quality Biological, Inc., Phamphlet entitled "Serum–Free Media Development"(1995).

Quality Biological, Inc., Information Sheets for QBSF–60 entitled "Products For Hematopoietic Cell Culture" (2 sheets).

StemPro–34 SFM Promotional Material, 3 pp. (Mar. 1996).

Life Technologies Catalog, pp. 3–4 to 3–6 (1997).

Biowhittaker Catalog for X–Vivo 15 and X–Vivo 20 Products, 5 pages (1996).

*Primary Examiner*—Sandra E. Saucier
*Assistant Examiner*—Vera Afremova
*Attorney, Agent, or Firm*—Birch, Stewart, Kolasch & Birch

[57] ABSTRACT

A serum-free medium which supports the proliferation and differentiation of CD34+ cells purified from normal bone marrow, peripheral blood of patients treated with cytokines, and umbilical cord blood is described. The recipe for the formulation is given, which provides a medium suitable for the proliferation and differentiation of CD34+ cells for use in human therapeutic protocols.

17 Claims, No Drawings

METHOD FOR CULTURING CD34+ CELLS IN A SERUM-FREE MEDIUM

This application claims priority on provisional application Ser. No. 60/028,152 filed on Oct. 18, 1996, the entire contents of which are hereby incorporated by reference.

This invention was made with Government support under Contract No. HL 53804 awarded by the National Institute of Heart, Lung and Blood. The Government has certain rights in the invention.

BACKGROUND OF THE INVENTION

The present invention relates to a serum-free medium which can support the growth and proliferation of normal human hematopoietic CD34+ cells purified from sources such as normal human bone marrow, the peripheral blood of patients treated with cytokines (termed mobilized CD34+ cells) or umbilical cord blood.

The growth of these cells is becoming more important in view of recent developments in clinical regimens for combatting diseases such as cancer, myeloproliferative diseases and autoimmune diseases. However, many media are not suitable for culturing normal bone marrow cells, especially CD34+ cells because of their high proliferative capability. Therefore, a need exists for developing a serum-free medium which can support the proliferation and differentiation of CD34+ cells.

SUMMARY OF THE INVENTION

Since not all cells will proliferate in a single (universal) serum-free medium, care must be taken in the development of each medium. Such a medium is invaluable in the expansion of specific hematopoietic lineages for bone marrow transplantation. Such a medium will allow the potential to store small amounts of bone marrow or subsets of the bone marrow cell population (such as by freezing) and at a later time expand the cells by thawing the cells and growing them in vitro for transplantation purposes. The inventor has developed such a medium that can support CD34+ cellular proliferation and in the presence of the appropriate cytokine(s), expand specific cell types/lineages. An advantage to this medium is that it contains components derived from U.S. Pharmaceutical grade components that will permit it to be used in clinical regimens.

It is one object of the invention to provide a serum-free medium comprising a basal medium, an effective amount of essential fatty acid, an effective amount of cholesterol, transferrin in an amount of 120 to 500 μg/ml or an effective amount of an iron salt and an effective amount of insulin growth factor, wherein said medium supports the proliferation and differentiation of normal CD34+ cells or comprising a basal medium, an effective amount of fatty acid, an effective amount of cholesterol, an effective amount of transferrin or an effective amount of an iron salt and insulin in an amount of 0.25 to 2.5 U/ml or an effective amount of insulin like growth factor, wherein said medium supports the proliferation and differentiation of normal CD34+ cells.

It is another object of the invention to provide a serum-free medium comprising a serum-free culture medium which supports the proliferation and differentiation of CD34+ cells which comprises an effective amount of human serum albumin, transferrin in an amount of 130 to 500 μg/ml and insulin in an amount of 0.25 to 2.5 U/ml, wherein said human serum albumin, transferrin, and insulin are each present in an amount effective for supporting the proliferation and differentiation of CD34+ cells.

It is another object of the invention to provide a method for growing normal CD34+ cells which comprises cultivating said cells in one of the above defined media or in a serum-free medium comprising: human serum albumin; transferrin; and insulin, wherein each of said human serum albumin, transferrin and insulin is dissolved in a serum-free basal medium.

Various growth factors and/or cytokines for driving proliferation and differentiation of the cells can optionally be added to the medium used to culture the cells. By means of adding various cytokines, the composition of the cell population can be altered with respect to the types of cells present in the population.

DETAILED DESCRIPTION OF THE INVENTION

The term "serum-free" is used herein to mean that all whole serum is excluded from the medium. Certain purified serum components, such as human serum albumin, can be added to the medium.

Basal medium

The basal medium is preferably Iscove's modified Dulbecco's medium (IMDM). Other such basal media might be used, such as McCoy's 5a or a blend of Dulbecco's modified Eagle's Medium and Ham's-F12 media at a 1:1 ratio. The requirements of the basal medium are that it provide i) inorganic salts so as to maintain cell osmolality and mineral requirements (e.g., potassium, calcium, phosphate, etc.), ii) essential amino acids required for cell growth, that is, amino acids not made by endogenous cellular metabolism, iii) a carbon source which can be utilized for cellular energy metabolism, typically glucose, and iv) various vitamins and co-factors, such as riboflavin, nicotinamide, folic acid, choline, biotin, and the like, as my be required to sustain cell growth. Glutamine is one of the amino acids which may be added to the medium of the present invention in an effective amount. The glutamine concentration is usually between 100 and 500 μg/ml, preferably between 125 and 375 μg/ml and most preferably between 150 and 300 μg/ml. Because of its instability, glutamine is sometimes added just before use of the media.

The basal medium also typically contains a buffer to maintain the pH of the medium against the acidifying effects of cellular metabolism, usually bicarbonate or HEPES. The pH of the basal medium is usually between 6.8 and 7.2. The composition of IMDM is shown in Table I, below:

TABLE I

Iscove's Modified Dulbecco's Medium

| Component | mg/L |
|---|---|
| L-Alanine | 25.0 |
| L-Arginine HCl | 84.0 |
| L-Asparagine.H$_2$O | 28.40 |

TABLE I-continued

Iscove's Modified Dulbecco's Medium

| Component | mg/L |
|---|---|
| L-Aspartic Acid | 30.0 |
| L-Cystine.2HCl | 91.24 |
| L-Glutamic Acid | 75.0 |
| L-Glutamine | 584.0 |
| Glycine | 30.0 |
| L-Histidine HCl.H$_2$O | 42.0 |
| L-Isoleucine | 104.8 |
| L-Leucine | 104.8 |
| L-Lycine HCl | 146.2 |
| l-Methionine | 30.0 |
| L-Phenylalanine | 66.0 |
| L-Proline | 40.0 |
| L-Serine | 42.0 |
| L-Threonine | 95.2 |
| L-Tryptophan | 16.0 |
| L-Tyrosine, 2Na.2H$_2$O | 103.79 |
| L-Valine | 93.6 |
| Biotin | 0.013 |
| D-Ca Pantothenate | 4.00 |
| Choline Chloride | 4.00 |
| Folic Acid | 4.00 |
| i-Inositol | 7.00 |
| Nicotinamide | 4.00 |
| Pyridoxal HCl | 4.00 |
| Riboflavin | 0.40 |
| Thiamine HCl | 4.00 |
| Vitamin B$_{12}$ | 0.013 |
| Antibiotics | omitted |
| 2-a-Thioglycerol (7.5E-5M) | omitted |
| CaCl$_2$.2H$_2$O | 215.86 |
| KCl | 330.0 |
| KNO$_3$ | 0.076 |
| MgSO$_4$ (anhyd) | 97.67 |
| NaCl | 4505. |
| NaH$_2$PO$_4$ | 108.69 |
| Na$_2$SeO$_3$.5H$_2$O | 0.0173 |
| Glucose | 4500. |
| Phenol Red.Na | 15.34 |
| Sodium Pyruvate | 110.0 |
| NaHCO$_3$ | 3024. |
| HEPES 25 mM | 5958. |
| CO$_2$ (The air in the jar over the medium contains 5% CO$_2$ and air) | 5% |

Albumin

Albumin is preferably supplied in the form of human serum albumin (HSA) in an effective amount for the growth of cells. HSA provides a source of protein in the media. Moreover, protein acts as a substrate for proteases which might otherwise digest cell membrane proteins. Albumin is thought to act as a carrier for trace elements and essential fatty acids. HSA is greatly advantageous over protein derived from animals such as bovine serum albumin (BSA) due to the reduced immunogenic potential of HSA. The HSA may be derived from pooled human plasma fractions, or may be recombinantly produced in such hosts as bacteria and yeast, or in vegetable cells such as potato and tomato. Preferably, the HSA used in the present formulations is free of pyrogens and viruses, and is approved regulatory agencies for infusion into human patients. The HSA may be deionized using resin beads prior to use. The concentration of human serum albumin is 1–8 mg/ml, preferably 3–5 mg/ml, most preferably 4 mg/ml.

Soluble carrier/Fatty acid complex

The albumin mentioned above could be substituted by a soluble carrier/essential fatty acid complex and a soluble carrier cholesterol complex which can effectively deliver the fatty acid and cholesterol to the cells. An example of such a complex is a cyclodextrin/linoleic acid, cholesterol and oleic acid complex. This is advantageous as it would allow for the replacement of the poorly characterized albumin with a well defined molecule. The use of cyclodextrin removes the need for the addition of human/animal serum albumin, thereby eliminating any trace undesired materials which the albumin would introduce into the media. The use of cyclodextrin simplifies the addition of specific lipophilic nutrients to a serum-free culture.

Three cyclodextrins which are employable are α-, β-, and γ-cyclodextrins. Among them, β-cyclodextrin appears to be the best. In this invention dealing with the expansion of CD34$^+$ cell, the use of human serum albumin can be replaced by the addition of β-cyclodextrin complexed with linoleic acid, cholesterol and oleic acid. However, in other embodiments, any cyclodextrin can be used to include numerous lipophilic substances to the culture.

The lipophilic substances which can be complexed with cyclodextrin include unsaturated fatty acids such as linoleic acid, cholesterol and oleic acid. The linoleic acid, cholesterol and oleic acid are present in effective amounts and can be present in equal proportions such that the total amount is 0.001 to 100 μg/ml, preferably 0.1 to 10 μg/ml. The preparation of such complexes is known in the art and is described, for example, in U.S. Pat. No. 4,533,637 of Yamane et al, the entire contents of which is hereby incorporated by reference.

Iron Source

A source of iron in an effective amount and in a form that can be utilized by the cells can be added to the media. The iron can be supplied by transferrin in an effective amount. The transferrin may be derived from animal sera or recombinantly synthesized. It is understood that when transferrin is derived from an animal source, it is purified to remove other animal proteins, and thus is usually at least 99% pure. The transferrin concentration is usually between 80 and 500 μg/ml, preferably between 120 and 500 μg/ml, more preferably between 130 and 500 μg/ml, even more preferably between 275 and 400 μg/ml and most preferably 300 μg/ml. Alternatively, an iron salt, preferably a water soluble iron salt, such as iron chloride (e.g. FeCl$_3$.6H$_2$O) dissolved in an aqueous solution such as an organic acid solution (e.g. citric acid) can be used to supply the iron. One mole of iron chloride is usually used for every mole of citric acid. The concentration of iron chloride is 0.0008 to 8 μg/ml, preferably 0.08 to 0.8 μg/ml, most preferably 0.08 μg/ml.

Insulin Growth Factor

Insulin may also be added to the media of the present invention in an effective amount. The insulin concentration is between 0.25 and 2.5 U/ml, more preferably 0.4–2.1 U/ml, most preferably 0.48 U/ml. In the conversion of Units to mass, 27 U=1 mg. Therefore, incorporating the conversion, the insulin concentration is approximately between 9.26 μg/ml and 92.6 μg/ml, more preferably 14.8 μg/ml–77.8 μg/ml, most preferably 17.7 μg/ml. It is again understood that human insulin is more preferable than animal insulin. Highly purified recombinant insulin is most preferred. An insulin like growth factor such as insulin like growth factor 1 and insulin like growth factor 2 may be used in place of insulin in an amount which provides substantially the same result as a corresponding amount of insulin. Thus, the term "insulin growth factor" includes both insulin and insulin like growth factors.

Additional components

The addition of other lipids to the above essential reagents could enhance the proliferative potential of precursor cells. These components, however, are preferably not added unless they are necessary for a particular experiment or to grow a particular type of cell. Optionally, triglycerides and/or phospholipids may be included as additional sources of lipid. A preferable source of lipid contains a mixture of neutral triglycerides of predominantly unsaturated fatty acids such as linoleic, oleic, palmitic, linolenic, and stearic acid. Such a preparation may also contain phosphatidylethanolamine and phosphatidylcholine. Another source of lipid is a human plasma fraction precipitated by ethanol and preferably rendered virus free by pasteurization.

Other ingredients which can optionally be added to the media are cited in the following references: Smith et al, WO 95/06112, Yamane et al, U.S. Pat. No. 4,533,637, Ponting et al, U.S. Pat. No. 5,405,772. The entire contents of all of these references are incorporated by reference.

Undesired components

When the media is to be used to grow cells for introduction into a human patient, the media preferably does not contain ingredients such as bovine serum albumin, mammalian serum, and/or any natural proteins of human or mammalian origin (as explained above). It is preferable that recombinant or synthetic proteins, if they are available and of high quality, are used. Most preferably, the amino acid sequences of the recombinant or synthetic proteins are identical to or highly homologous with those of humans. Thus, the most preferable serum-free media formulations herein contain no animal-derived proteins and do not have even a non-detectable presence of animal protein.

In the most ideal system, optional components which are not necessary are preferably not added to the medium. Such optional components are described in the prior art cited above and may be selected from the group consisting of meat extract, peptone, phosphatidylcholine, ethanolamine, anti-oxidants, deoxyribonucleosides, ribonucleosides, soy bean lecithin, corticosteroids, and EX-CYTE, myoinositol, monothioglycerol, and bovine or other animal serum albumin.

Preparation

The medium of the present invention is of course aqueous and is made using distilled water. The medium is formulated from freely soluble materials. Thus, the order of the addition of the ingredients is not particularly important to the invention. Typically, the basal medium is made first and the remaining components required for growth of bone marrow cells in the absence of serum are then added to the basal medium.

The most ideal system, as described in this invention, is one wherein the serum-free media is made fresh on the day that it is to be added to the culture. However, when storage previous to use is necessary, it may be desirable to add certain compounds. Reducing agents such as α-monothioglycerol and β-mercaptoethanol, which are thought to diminish free-radical formation, may be added to the serum-free media formulations. This will enhance stability of the serum-free media during storage for lengths of time of up to 20 days or longer. Additionally, in these less than preferred circumstances, antibiotics may also be added to the media as a precaution against bacterial contamination.

All of the ingredients in the medium, including the ingredients in the basal medium, are present in amounts sufficient to support the proliferation and differentiation of $CD34^+$ cells. If a basal medium is made which comprises IMDM reformulated with respect to the amounts of the components of IMDM, it is expected that the reformulation will contain those essential components of IMDM in amounts 0.1 to 10, preferably 0.5 to 2 times, most preferably 0.8 to 1.2 times their amounts in the formulation IMDM described above.

The medium is formulated and sterilized in a manner conventional in the art. Typically, stock solutions of these components are made filter sterilized. A finished medium is usually tested for various undesired contaminants, such as mycoplasma or virus contamination, prior to use.

Utility

In the art of tissue culture it has for some time been desired that a serum-free medium be found that supports the proliferation and differentiation of $CD34^+$ cells. In part this is due to the desire of investigators to be able to study the effects of adding various components to a defined medium and thereby evaluate their role in hematopoiesis. Also, therapeutic regimes are being developed which depend upon bone marrow transplant techniques. Such transplants are useful in the therapy of radiation exposure, immunodeficiency and tumors of the hematopoietic system (leukemias). The media of the present invention can be used to cultivate mixed cell populations which contain $CD34^+$ cells to selectively enrich (increase the proportion of) $CD34^+$ cells in the population.

Recent studies have shown that an early progenitor/stem ($CD34^+$) cells can be highly purified and can differentiate into all the different hematopoietic linages in the presence of specific cytokines. These cells have been successfully used in the clinic for transplantation and has promise for use in gene therapy.

The medium of the present invention, a formulation suitable for use in human therapeutic protocols, has two types of utility in transplant therapies as described above. First, the media can be used in the expansion of the $CD34^+$ cells which are responsible for repopulating the host bone marrow. The media of the present invention can be used in the expansion of these early progenitor stem cells which can then be mixed with fresh unfractionated bone marrow and transplanted or transplanted alone. The rationale for this use is that the in vitro treatment allows for differentiation of the early progenitor cells to mature cells, capable of protecting the host from opportunistic diseases which occur during bone marrow transplantations.

In either of the above cases, the presence of appropriate growth factors, such as interleukins (IL), colony stimulating factors (CSF), and the like, will influence the rate of proliferation and the distribution of cell types in the population. Cytokines used for the expansion and differentiation of early progenitor cells are stem cell factor, interleukin-1 and interleukin-6. Cytokines used to stimulate proliferation and differentiation of mid-progenitor cells are interleukin-3 and granulocyte-macrophage colony stimulating factor. Cytokines which promote the differentiation of specific blood cell types are granulocyte colony stimulating factor, macrophage colony stimulating factor and erythropoietin. For transplantation purposes, the GM-colony forming cells are among the most important. The myeloid population is absolutely necessary for the transplant patient to survive. The role which each of these cytokines play in hematopoiesis is under intense investigation in the art and it is expected that eventually it will be possible to faithfully recapitulate hematopoiesis in vitro.

The second utility is in "ex-vivo purging" protocols. In a therapy of this type, "normal" (non-tumorigenic) $CD34^+$ cells that are tainted with tumor cells, either of bone marrow or metastatic origin, are placed into in vitro culture in the medium of the present invention. The mixture of normal bone marrow cells and tumor cells is then treated with reagents which are preferentially cytotoxic for the tumor cells. Alternatively, the tumor cells can be selectively depleted from the culture using immobilized antibodies which specifically bind to the tumor cells. The "purged" bone marrow is then transplanted back into the patient. The media of the present invention is suitable for storing the cells when they are removed from the human body and is also particularly useful for growing the cells when they are removed from the human body. The medium is especially adapted to selectively promote the growth of $CD34^+$ cells so that a mixed culture of cells can be enriched in $CD34^+$ cells and the $CD34^+$ cells can be returned to a patient in need of the cells. The media is also useful for growing $CD34^+$ cells after they halve been separated from other cells. After the $CD34^+$ cells have been grown to increase the number of cells, they can be given to a human patient for known therapies.

When supplemented with SCF, IL-3, IL-6 and G-CSF at 50ng/ml each, the media of the present invention can maintain a distinct population of cells with the immature $CD34^+/33^-$ phenotype. Additionally, when supplemented with heparin (10 µg/ml), hydrocortisone (2.0 µg/ml), rhFGF-$\beta$ (1 ng/ml), rhEGF (10 µg/ml), and rhECGF (0.6 ng/ml), tha media of the present invention can support the proliferation of human larger vessel endothelial cells. This proliferation is comparable to that experienced with serum-containing media. Also, the media of the present invention can support the proliferation of human peripheral blood lymphocytes. To accomplish this, human peripheral blood lymphocytes are cultured in the media of the present invention which is supplemented with phytohemagglutinin (1.0 µg/ml) and optionally IL-2 (5 U/ml) for 4–7 days. After this original culture period, the human peripheral blood lymphocytes are then cultured in the media of the present invention which is supplemented with IL-2 (5 U/ml) only. This proliferation is also comparable to that experienced with serum-containing media.

The invention is illustrated by the Examples below, which are not intended to be limiting of the scope of the invention.

EXAMPLE I

In order to develop a medium that can be used for human clinical $CD34^+$ cell regimens, the components of media developed for unfractionated bone marrow needed to be optimized with U.S. Pharmaceutical grade components. The serum-free media of this example is composed of the basal medium IMDM plus the following additives, 2 mM L-glutamine, 100 U/ml penicillin, 100 µg/ml streptomycin and the serum-free components: human injectable grade serum albumin (4 mg/ml) (Alpha Therapeutic Corporation), partially iron saturated human transferrin (300 µg/ml) (Sigma Chemical Corporation or Bayer Corporation) and human recombinant sodium insulin (0.48 U/ml) (Sigma). Since L-glutamine present in IMDM is unstable, additional glutamine was added to the medium. The medium can be changed every 1–7 days, preferably every 2–7 days, more preferably every 3–7 days and most preferably every 7 days. The medium is changed often enough to allow the $CD34^+$ cells to grow and proliferate. Unnecessary changing of the media is avoided because of extra time and expense and risk of contamination.

In the experiments in this Example, the Serum Free Media 1 and Serum Free Media 2 had the same compositions of ingredients except as described below.

|  | Serum Free Media 1 |  | Serum Free Media 2 |  |
|---|---|---|---|---|
| Insulin | 0.48 | U/ml | 0.14 | U/ml |
| Transferrin | 300 | µg/ml | 100 | µg/ml |

The data in Table II illustrates that in three separate experiments using $CD34^+$ cells purified from three individual normal human bone marrow aspirates proliferated in the presence of the cytokines, SCF, IL-3, IL-6 and G-CSF (50 ng/ml each) plus the serum-free medium 1, Serum Free Medium 2, or serum-containing medium to nearly equivalent levels after 14 days of culture. However, in the presence of the above cytokines plus the Serum Free Medium 2, Serum Free Medium 1, (developed especially for the $CD34^+$ cells) the $CD34^+$ cells proliferated to significantly higher levels than the other media by day 14.

TABLE II

Proliferation of $CD34^+$ cells purified from normal bone marrow cultured for 14 days in Serum Free Medium 1, Serum Free Medium 2 and serum-containing medium each supplemented with the cytokines; SCF, IL-3, IL-6 and G-CSF at 50 ng/ml each. The data is from three separate experiments using $CD34^+$ cells from three different donors. The spent medium and cytokines were replaced with fresh medium and cytokines every 7 days.

|  | Medium | Initial Seeding Density $\times 10^4$/ml | Day 14 Density $\times 10^4$/ml |
|---|---|---|---|
| Expt. 1 | Serum Free Medium 1 | 2 | 95 |
|  | Serum Free Medium 2 | 2 | 60 |
|  | IMDM + 20% FBS | 2 | 78 |
| Expt. 2 | Serum Free Medium 1 | 2 | 140 |
|  | Serum Free Medium 2 | 2 | 36 |

TABLE II-continued

Proliferation of CD34+ cells purified from normal bone marrow cultured for 14 days in Serum Free Medium 1, Serum Free Medium 2 and serum-containing medium each supplemented with the cytokines; SCF, IL-3, IL-6 and G-CSF at 50 ng/ml each. The data is from three separate experiments using CD34+ cells from three different donors. The spent medium and cytokines were replaced with fresh medium and cytokines every 7 days.

|  | Medium | Initial Seeding Density x10$^4$/ml | Day 14 Density x10$^4$/ml |
|---|---|---|---|
|  | IMDM + 20% FBS | 2 | 14 |
| Expt. 3 | Serum Free Medium 1 | 2 | 100 |
|  | Serum Free Medium 2 | 2 | 62 |
|  | IMDM + 20% FBS | 2 | 52 |

In another experiment we compared the Serum Free Medium 1 with Serum Free Medium 2, serum-containing medium and three commercially available serum-free media developed especially for hematopoietic cells. The CD34+ cells were cultured from an initial seeding level of 2×10$^4$ for 14 days in each of the above medium plus cytokines. Again, the Serum Free Medium 1 performed the best, supporting CD34+ cellular proliferation to 100×10$^4$ cells/ml, whereas, Serum Free Medium 2 and IMDM plus 20% FBS supported cellular proliferation to 62×10$^4$/ml and 52×10$^4$/ml respectively. Two serum-free formulations developed especially for lymphocytes, AIM V (Life Technologies) and X-VIVO 10 (BioWhittaker) only supported the CD34+ proliferation to 36×10$^4$/ml and 60×10$^4$ cells/ml respectively. Proliferation of the CD34+ cells in StemPro 34 (Life Technologies) (a serum-free formulation designed especially for CD34+ cells) only supported the proliferation of the CD34+ cells to 30×10$^4$ cells/ml.

TABLE III

Proliferation of CD34+ cells purified from normal human bone marrow and cultured for 14 days in various media plus the cytokines SCF, IL-3, IL-6 and G-CSF at 50 ng/ml each. The spent medium and cytokines were replaced with fresh medium and cytokines every 7 days.

| Medium | Initial Seeding Level x10$^4$/ml | Day 14 Density x10$^4$/ml |
|---|---|---|
| Serum Free Medium 1 | 1 | 100 |
| Serum Free Medium 2 | 1 | 62 |
| IMDM + 20% FBS | 1 | 52 |
| AIM V | 1 | 36 |
| X-VIVO 10 | 1 | 60 |
| StemPro 34 | 1 | 30 |

Table IV illustrates that mobilized CD34+ cells cultured for 14 days in Serum Free Medium 1 or IMDM +20% FBS plus the above noted cytokines proliferated to equivalent levels in three separate experiments. Again, the commercially available serum-free medium, StemPro 34 containing the noted cytokines did not support the proliferation of CD34+ cells to the same level as Serum Free Medium 1 plus the added cytokines.

TABLE IV

Proliferation of mobilized CD34+ cells after 14 days of culture in the noted medium containing the cytokines SCF, IL-3, IL-6 and G-CSF at 50 ng/ml each. The data is from three separate experiments using CD34+ cells. The spent medium and cytokines were replaced with fresh medium and cytokines every 7 days.

|  | Medium | Initial Seeding Density x10$^4$/ml | Day 14 Density x10$^4$/ml |
|---|---|---|---|
| Expt. 1 | Serum Free Medium 1 | 2 | 132 |
|  | Serum Free Medium 2 | 2 | 80 |
|  | IMDM + 20% FBS | 2 | 132 |
| Expt. 2 | Serum Free Medium 1 | 2 | 90 |
|  | StemPro 34 | 2 | 62 |
|  | IMDM + 20% FBS | 2 | 100 |
| Expt. 3 | Serum Free Medium 1 | 2 | 180 |
|  | StemPro 34 | 2 | 32 |
|  | IMDM + 20% FBS | 2 | 170 |

In another experiment we compared the Serum Free Medium 1 and IMDM plus 20% FBS both containing the added cytokines for the ability to support the growth of CD34+ cells purified from umbilical cord blood (Table V). After 14 days of culture the CD34+ cells cultured in Serum Free Medium 1 proliferated from 2×10$^4$/ml to 200×10$^4$/ml, whereas the CD34+ cells cultured in the serum-containing medium proliferated only from 2×10$^4$/ml to 129×10$^4$/ml.

In another experiment using cord blood CD34+ cells, Serum-Free Medium 1 supported the proliferation from an initial seeding level of 1×10$^4$/ml to 186×10$^4$/ml, whereas, Serum-Free Medium 2 and IMDM+20% FBS supported the proliferation from 1×10$^4$/ml to 153×10$^4$/ml and 134×10$^4$/ml, respectively. Two commercially available serum-free medium designed for lymphocytes, AIM V and X-VIVO 10, supported cord blood CD34+ cell proliferation from 1×10$^4$/ml to 49×10$^4$/ml and 123×10$^4$/ml, respectively. The commercially available serum-free medium designed for CD34+ cells supported the proliferation of the cord blood CD34+ cells from 1×10$^4$/ml to only 88×10$^4$/ml. This again illustrates the ability of the Serum-Free Medium 1 to support the proliferation of CD34+ cells derived from umbilical cord blood to higher levels than serum-containing medium or any other commercially available serum-free medium designed especially for hematopoietic cells.

TABLE V

Proliferation of cord blood CD34$^+$ cells after 14 days of culture in the noted medium containing the cytokines; SCF, IL-3, IL-6 and G-CSF at 50 ng/ml each. The spent medium and cytokines were replaced with fresh medium and cytokines every 7 days.

|  | Medium | Initial Seeding Density x10$^4$/ml | Day 14 Density x10$^4$/ml |
|---|---|---|---|
| Expt. 1 | Serum-Free Medium 1 | 2 | 200 |
|  | IMDM + 20% FBS | 2 | 129 |
| Expt. 2 | Serum-Free Medium 1 | 1 | 186 |
|  | Serum-Free Medium 2 | 1 | 153 |
|  | IMDM + 20% FBS | 1 | 134 |
|  | Stem Pro | 1 | 88 |
|  | AIM V | 1 | 49 |
|  | X-VIVO 10 | 1 | 123 |
| Expt. 1 | Serum-Free Medium 1 | 2 | 200 |
|  | IMDM + 20% FBS | 2 | 129 |
| Expt. 2 | Serum-Free Medium 1 | 1 | 186 |
|  | Serum-Free Medium 2 | 1 | 153 |
|  | IMDM + 20% FBS | 1 | 134 |
|  | Stem Pro | 1 | 88 |
|  | AIM V | 1 | 49 |
|  | X-VIVO 10 | 1 | 123 |

The medium of the present invention has several advantages. First, the medium of the present invention is useful in the growth of CD34$^+$ cells for human therapeutic protocols. Second, all of the components of the media of the present invention are freely soluble in water, making formulation of the medium very easy. No component need be prepared as a stock solution in an organic solvent, which upon dilution in the media might cause precipitation of some components.

The invention being thus described, various modifications of the materials and methods set forth will be obvious to one of skill in the art. Such modifications are within the scope of the invention as defined by the claims below.

What is claimed is:

1. A method for preparing an enriched normal CD34$^+$ cell population, which comprises:
   cultivating said cells in a serum-free medium comprising: human serum albumin, transferrin in an amount of 130–500 μg/ml, and insulin in an amount of 0.4 to 2.1 U/ml, wherein each of said human serum albumin, transferrin and insulin is dissolved in a serum-free basal medium; and
   enriching the CD34$^+$ cells by removing CD34$^+$ cells from non-CD34$^+$ cells, either before, during and/or after said cultivation to prepare said enriched normal CD34$^+$ cell population.

2. The method of claim 1, wherein said medium further comprises at least one cytokine.

3. The method of claim 2, wherein said cytokine is selected from the group consisting of stem cell factor, interleukin-1, interleukin-3, interleukin-6, granulocyte-macrophage colony stimulating factor, granulocyte colony stimulating factor, macrophage stimulating factor and erythropoietin.

4. The method of claim 1, wherein said medium is replaced at intervals of 3–7 days.

5. A method for growing CD34$^+$ cells, which comprises:
   cultivating a mixed human bone marrow cell population, containing CD34$^+$ cells and non-CD34$^+$ cells in the population, in a serum-free culture medium, comprising:
   a basal medium,
   an effective amount of essential fatty acids,
   an effective amount of cholesterol,
   transferrin in an amount of 130 to 500 μg/ml, and
   an effective amount of insulin growth factor, wherein said effective amounts in the medium are sufficient to support the proliferation and differentiation of normal CD34$^+$ cells, and wherein the cultivating is under conditions which increase the proportion of CD34$^+$ cells in the population.

6. A method for growing CD34$^+$ cells, which comprises:
   cultivating a mixed human bone marrow cell population, containing CD34$^+$ cells and non-CD34$^+$ cells in the population, in a serum-free culture medium comprising:
   a basal medium,
   an effective amount of fatty acid,
   an effective amount of cholesterol,
   transferrin in an amount of at least 130 μg/ml, and
   insulin in an amount of 0.25 to 2.5 U/ml or an effective amount of insulin like growth factor, wherein said effective amounts in the medium are sufficient to support the proliferation and differentiation of normal CD34$^+$ cells, and wherein the cultivating is under conditions which increase the proportion of CD34$^+$ cells in the population.

7. A method for growing CD34$^+$ cells, which comprises:
   cultivating a mixed human bone marrow cell population, containing CD34$^+$ cells and non-CD34$^+$ cells in the population, in a serum-free culture medium comprising:
   a basal medium,
   an effective amount of essential fatty acids,
   an effective amount of cholesterol,
   transferrin in an amount of 130 to 500 μg/ml, and
   insulin in an amount of 0.4 to 2.1 U/ml; wherein said effective amounts in the medium are sufficient to support the proliferation and differentiation of normal CD34$^+$ cells, and wherein the cultivating is under conditions which increase the proportion of CD34$^+$ cells in the population.

8. The method of claim 7 wherein the medium further comprises at least one cytokine.

9. A method for growing CD34+ cells which comprises cultivating said cells in a serum-free culture medium comprising:
   a basal medium,
   an effective amount of essential fatty acids,
   an effective amount of cholesterol,
   transferrin in an amount of 130 to 500 μg/ml, and
   an effective amount of insulin growth factor, wherein said effective amounts in the medium are sufficient to support the proliferation and differentiation of normal CD34$^+$ cells.

10. A method for growing CD34+ cells which comprises cultivating said cells in a serum-free culture medium comprising:

an effective amount of fatty acid, an effective amount of cholesterol, transferrin in an amount of at least 130 μg/ml, and insulin in an amount of 0.25 to 2.5 U/ml or an effective amount of insulin like growth factor, wherein said effective amounts in the medium are sufficient to support the proliferation and differentiation of normal CD34+ cells.

11. A method for growing CD34$^+$ cells which comprises cultivating said cells in a serum-free culture medium which supports the proliferation and differentiation of CD34$^+$ cells which comprises:

a basal medium, an effective amount of human serum albumin, transferrin in an amount of 130 to 500 μg/ml, and insulin in an amount of 0.25 to 2.5 U/ml, wherein said human serum albumin, transferrin, and insulin are each present in an amount effective for supporting the proliferation and differentiation of CD34$^+$ cells.

12. The method of claim 11 wherein the medium does not further comprise lipids.

13. The method of claims 9 or 10, wherein the CD34+ cells are derived from a human peripheral blood cell population or a cord blood stem cell population.

14. The method of claim 11 wherein the CD34+ cells are derived from a human peripheral blood cell population.

15. The method of claim 11 wherein the CD34+ cells are derived from a cord blood stem cell population.

16. The method of claim 14, which further comprises enriching the CD34$^+$ cells by removing CD34$^+$ cells from non-CD34$^+$ cells, either before, during and/or after said cultivation.

17. The method of claim 15, which further comprises enriching the CD34$^+$ cells by removing CD34$^+$ cells from non-CD34$^+$ cells, either before, during and/or after said cultivation.

* * * * *